(12) United States Patent
Hillebrand

(10) Patent No.: US 9,222,084 B2
(45) Date of Patent: Dec. 29, 2015

(54) METHOD FOR ISOLATING PARALLEL DOUBLE AND SINGLE-STRANDED NUCLEIC ACIDS AND FOR SELECTIVELY REMOVING DOUBLE-STRANDED NUCLEIC ACIDS FROM A MIXTURE OF DOUBLE AND SINGLE-STRANDED NUCLEIC ACIDS

(75) Inventor: Timo Hillebrand, Hoenow (DE)

(73) Assignee: AJ Innuscreen GmbH, Berlin (DE)

( * ) Notice: Subject to any disclaimer, the term of this patent is extended or adjusted under 35 U.S.C. 154(b) by 707 days.

(21) Appl. No.: 12/349,095

(22) Filed: Jan. 6, 2009

(65) Prior Publication Data

US 2009/0234112 A1 Sep. 17, 2009

Related U.S. Application Data

(63) Continuation of application No. PCT/EP2007/056879, filed on Jul. 6, 2007.

(30) Foreign Application Priority Data

Jul. 6, 2006 (DE) .......................... 10 2006 031 764

(51) Int. Cl.
*C08B 37/00* (2006.01)
*C12N 15/10* (2006.01)

(52) U.S. Cl.
CPC .................................. *C12N 15/1006* (2013.01)

(58) Field of Classification Search
None
See application file for complete search history.

(56) References Cited

U.S. PATENT DOCUMENTS

| 5,155,018 | A | 10/1992 | Gillespie et al. | |
|---|---|---|---|---|
| 6,180,778 | B1* | 1/2001 | Bastian et al. | 536/25.4 |
| 2001/0041332 | A1* | 11/2001 | Hillebrand et al. | 435/6 |
| 2002/0081619 | A1* | 6/2002 | Bastian et al. | 435/6 |
| 2003/0039974 | A1* | 2/2003 | Skouv | 435/6 |
| 2003/0091989 | A1* | 5/2003 | Davis et al. | 435/5 |
| 2003/0096229 | A1* | 5/2003 | Bavykin et al. | 435/6 |
| 2003/0138828 | A1* | 7/2003 | Bost et al. | 435/6 |
| 2005/0032105 | A1* | 2/2005 | Bair et al. | 435/6 |
| 2005/0059054 | A1* | 3/2005 | Conrad et al. | 435/6 |
| 2005/0208510 | A1* | 9/2005 | Latham et al. | 435/6 |

FOREIGN PATENT DOCUMENTS

| EP | 1 146 049 | 10/2001 |
|---|---|---|
| WO | WO 97/28171 | 8/1997 |
| WO | WO 97/30152 | 8/1997 |
| WO | WO 9951734 A1 * | 10/1999 |

OTHER PUBLICATIONS

Janssen et al. Citrate versus heparin anticoagulation in chronic haemodialysis patients. Nephrol Dial Transplant 8:1228-1233 (1993).*
Aerosil® [online][retrieved on Mar. 14, 2015] retrieved from https://www.aerosil.com/lpa-productfinder/page/productsbytext/detail.html?pid=1830.*
Berger et al (Methods in Enzymology 180:3-13, 1989).*
U.S. Appl. No. 12/857,299, filed Aug. 16, 2010, Hillebrand, et al.
U.S. Appl. No. 12/352,170, filed Jan. 12, 2009, Hillebrand.
Schenk, J. A. et al., "Fast Isolation of RNA to Detect Expression of Tumor Markers", XP-000982430, Journal of Clinical Laboratory Analysis 11:340-342 (1997).
Gribanov et al, "Simple method for isolation and purification of RNA", *Bioorganicheskaya Khimiya*, 1997, vol. 23, No. 9, pp. 763-765 (w/English translation).

* cited by examiner

*Primary Examiner* — Samuel Woolwine
(74) *Attorney, Agent, or Firm* — Oblon, McClelland, Maier & Neustadt, L.L.P.

(57) ABSTRACT

A method for i) parallel isolation of a double-stranded and/or a single-stranded nucleic acid and/or ii) selective removal of a double-stranded nucleic acid from a mixture of a double-stranded and a single-stranded nucleic acid or from a source comprising a double-stranded and a single-stranded nucleic acid includes absorbing the double-stranded nucleic acid onto a first solid carrier, while the single-stranded nucleic acid is not adsorbed and remains in solution, removing the first carrier with the adsorbed nucleic acid from the solution, mixing the solution comprising the single-stranded nucleic acid with an alcoholic solution having a concentration of 1 to 90 vol.-%, and contacting the resulting solution with second solid carrier, to absorb the single-stranded nucleic acid onto the second solid carrier.

19 Claims, No Drawings

METHOD FOR ISOLATING PARALLEL DOUBLE AND SINGLE-STRANDED NUCLEIC ACIDS AND FOR SELECTIVELY REMOVING DOUBLE-STRANDED NUCLEIC ACIDS FROM A MIXTURE OF DOUBLE AND SINGLE-STRANDED NUCLEIC ACIDS

BACKGROUND OF THE INVENTION

1. Field of the Invention

The invention relates to a method for efficient and extremely simple and cost-advantageous parallel isolation of double-stranded and single-stranded nucleic acids.

2. Discussion of the Background

The parallel isolation of genomic DNA and cellular total RNA from a biological sample is connected with only a few practicable methods at the present time. A method for the separation of genomic DNA and cellular total RNA by way of selective precipitation steps, using lithium chloride, is described by Raha, S., Merante, F., Proteau, G. and Reed, J. K. (GATA, 1990, 7(7): 173-177). Another possibility for parallel isolation of DNA and RNA utilizes ultra filtration techniques, using a cesium chloride gradient for pelleting the RNA, in combination with subsequent dialysis of the DNA (Coombs, L. M., Pigott, D., Proctor, A., Eydmann, M., Denner, J. and Knowles, M. A.; Anal. Biochem. (1990); 188; 338-343). The published method is extremely time-consuming and requires a special effort in terms of apparatus.

A disadvantage of this method, however, is the complicated preparation steps and the use of highly toxic and carcinogenic substance groups such as chloroform and phenol. Finally, the time required is also very great.

A simplified method for simultaneous isolation of DNA and RNA is disclosed in the Laid Open patent application WO 97/28171 A1. Here, the biological sample is lysed using a chaotropic buffer. After lysis, the addition of nanoparticles (smaller than 40 nm) made of monodisperse silicon material takes place. The genomic DNA binds to these particles. The batch is then centrifuged. This causes the silicon particles to be pelletized. The excess is transferred to a new reaction vessel. The pelletized carrier material is subsequently washed with a washing buffer that contains ethanol, and the bound DNA is finally dissolved from the mineral carrier material again, using a low-salt buffer. The remaining excess is subjected to phenol/chloroform extraction, in traditional manner, and the RNA is finally precipitated in this way, and dissolved using water, after washing steps.

The method is faster than the method described above. However, in this method, as well, work is carried out with highly toxic and carcinogenic substance groups such as chloroform and phenol.

Another method for separation and isolation of single-stranded and double-stranded nucleic acids is disclosed in the patent EP 1 146 049 B1.

The method is based on the treatment of a source that contains nucleic acids, using at least one mineral carrier material, in such a form that 1. the single-stranded nucleic acid is isolated, in that the treatment conditions are adjusted by means of an aqueous mixture of chaotropic salts and low aliphatic alcohols, in such a manner that subsequently, the single-stranded nucleic acid is primarily adsorbed onto a mineral carrier, while the double-stranded nucleic acid is not adsorbed. The bound, single-stranded nucleic acid is subsequently washed and finally eluted from the carrier material by means of a low-salt buffer.

2. the double-stranded nucleic acid is isolated, in that the treatment conditions are adjusted by means of a mixture of substances that complex earth-alkali ions, without low aliphatic alcohols, in such a manner that subsequently, the double-stranded nucleic acid is primarily adsorbed onto a mineral carrier, while the single-stranded nucleic acid is not adsorbed. The bound, double-stranded nucleic acid is subsequently washed and finally eluted from the carrier material by means of a low-salt buffer.

3. the double-stranded nucleic acid is isolated in that the treatment conditions are adjusted by means of the presence of a sarcosinate but without low aliphatic alcohols, in such a manner that subsequently, the double-stranded nucleic acid is primarily adsorbed onto a mineral carrier, while the single-stranded nucleic acid is not adsorbed. The bound, double-stranded nucleic acid is subsequently washed and finally eluted from the carrier material by means of a low-salt buffer.

4. the double-stranded or single-stranded nucleic acid is isolated in that the treatment conditions are adjusted by means of an aqueous mixture of chaotropic salts and low aliphatic alcohols, in such a manner that both nucleic acid fractions adsorb onto a mineral carrier. Separation of the nucleic acids takes place by means of selective elution. In this connection, the double-stranded nucleic acid is dissolved from the carrier material by means of a solution having a reduced ion strength and low aliphatic alcohols. The remaining single-stranded nucleic acid is subsequently washed and finally dissolved from the carrier material by means of a low-salt buffer.

Alternatively to this, the single-stranded nucleic acid can be selectively eluted from the carrier material by means of a solution that contains substances that complex earth-alkali ions and/or contains sarcosinates. The now remaining double-stranded nucleic acid is subsequently washed, once again, and finally dissolved from the carrier material by means of a low-salt buffer.

The method is simple in its implementation, and does entirely without the use of phenol or chloroform. Also, time-consuming ethanol precipitation is not required.

However, it has also been shown that often, there is no selectivity of isolation of the nucleic acids, in each instance. For example, a commercially available extraction kit for isolation of RNA on the basis of the method described always requires DNase digestion. This is required since the selectivity for isolation of RNA solely with the method described, as presented, is not sufficient. The double-stranded DNA must additionally be removed by means of an enzymatic method.

WO 97/37040 A2 also refers to a method for separating single-stranded and double-stranded nucleic acids, particularly with regard to the isolation of HCV RNA from bodily fluids. As was already disclosed in EP 1 146 049 B1, binding of the double-stranded nucleic acid to a silica material also takes place in WO 97/37040 A2 in that the buffer used for this purpose requires a high concentration of EDTA (at least 100 mM). Thus, the presence of a complex-forming agent is required, at a high concentration, in order to bind double-stranded nucleic acid to mineral silica particles, and to prevent binding of single-stranded nucleic acid.

Thus, there has been a continued need for a method for efficient and extremely simple and cost-advantageous parallel isolation of double-stranded and single-stranded nucleic acids that avoids the above disadvantages.

DETAILED DESCRIPTION OF THE INVENTION

The present invention relates to a method for efficient and extremely simple and cost-advantageous parallel isolation of double-stranded and single-stranded nucleic acids. Double-stranded nucleic acid is particularly understood to be genomic DNA, and single-stranded nucleic acid is particularly understood to be RNA.

The present invention was based on the object of eliminating the disadvantages of the known methods, and of making available a better method for separation of single-stranded and double-stranded nucleic acids.

The method according to the present invention, for parallel isolation of double-stranded and single-stranded nucleic acids, as well as for selective removal of double-stranded nucleic acids from a mixture of double-stranded and single-stranded nucleic acids, or from sources containing these substances, comprises the following steps:

a) the lysed or homogenized sample is adjusted, in the absence of alcohol or substances that complex earth-alkali ions, or washing, dispersion, or wetting agents, using an aqueous saline solution in a concentration greater than 1M, in such a manner that the double-stranded nucleic acid is adsorbed onto a solid carrier, while the single-stranded nucleic acid is not adsorbed and remains in the solution, b) the carrier with the adsorbed nucleic acid is removed, c) the solution with the single-stranded nucleic acid is mixed with an alcoholic solution having a concentration of 1 to 90 vol.-% (preferably 20 to 80 vol.-%, even more preferably about 70 vol.-%), and brought into contact with another solid carrier, whereby the single-stranded nucleic acid is adsorbed onto this other carrier.

In a preferred embodiment, the nucleic acid adsorbed onto the solid carrier, in each instance, is washed and eluted according to known methods. The aqueous saline solution can comprise chaotropic or non-chaotropic salts, preferably guanidine salts. Preferably, a mineral carrier serves as the solid carrier. The solid carrier can be a component of a mini-centrifugation column.

According to a preferred embodiment, the same carrier material is used for adsorption of the double-stranded nucleic acid as for adsorption of the single-stranded nucleic acid.

Preferably, alcohols having 1 to 5 carbon atoms are used as the alcoholic solution. The alcoholic solution can additionally contain other substances, such as sodium acetate buffer or potassium acetate buffer, or an alcohol-detergent mixture, particularly non-ionic detergents.

A mineral carrier or magnetic iron oxide particles, preferably having modified surfaces, can be used for adsorption of the single-stranded nucleic acid.

Another object of the present invention is a kit for carrying out the method, which comprises the following components:
- an aqueous saline solution having a salt concentration greater than 1M, two solid carriers,
- an alcoholic solution with a concentration of 1 to 90 vol.-% (preferably 20 to 80 vol.-%, even more preferably about 70 vol.-%),
- washing and elution buffers, preferably known washing and elution buffers.

The aqueous saline solution is a solution of salts that do not form complexes.

The present invention thus also comprises the use of an aqueous saline solution having a salt concentration greater than 1M, for selective removal of double-stranded nucleic acids from a mixture of double-stranded and single-stranded nucleic acids, or from sources that contain these substances, by means of binding the double-stranded nucleic acids to a solid carrier.

Another object of the present invention is the use of an aqueous saline solution having a salt concentration greater than 1M for isolation of highly pure cellular total RNA, which is substantially free of genomic DNA (preferably completely free of genomic DNA), from a mixture of cellular total RNA and genomic DNA, or from sources that contain these substances, by means of binding the genomic DNA to a solid carrier.

According to the present invention, a method and a kit were made available, which make it possible to isolate double-stranded and single-stranded nucleic acids from a source that contains nucleic acids, in parallel, whereby the method is simple and quick in its implementation, and does entirely without the use of phenol or chloroform.

The method according to the present invention makes it possible to separate double-stranded and single-stranded nucleic acids from a source that contains nucleic acids, with the goal of selective separation of only the single-stranded nucleic acid, whereby again, the method is simple and quick in its implementation, and does entirely without the use of phenol or chloroform.

It was shown that it is possible to achieve separation of single-stranded and double-stranded nucleic acid in a completely different way from that described in the patent EP 1 146 049 B1. In EP 1 146 049 B1, two method alternatives were named for binding double-stranded nucleic acid to a solid carrier, namely:

1. buffers that contain a mixture of substances that complex earth-alkali ions, in other words EDTA, for example, or 2. buffers that contain a wetting, washing, or dispersion agent (sarcosinates).

In EP 1 146 049 B1, specifically these conditions—after incubation with a mineral carrier material—bring about selective binding of the double-stranded nucleic acid, whereby the single-stranded nucleic acid does not bind. The bound, double-stranded nucleic acid is subsequently washed, if necessary, and finally eluted from the mineral carrier material by means of low-salt buffer or water. The non-bound, single-stranded nucleic acid can then also be isolated, in that the binding conditions are adjusted, by means of adding an alcohol, for example, in such a manner that efficient adsorption to another mineral material takes place. The bound, single-stranded nucleic acid is also subsequently washed and finally, again dissolved from the mineral material.

Furthermore, it is mentioned in EP 1 146 049 B1 that in the case of addition of an aqueous mixture of chaotropic salts in a concentration greater than 1M and low aliphatic alcohols, the treatment conditions can be adjusted in such a manner that predominantly the single-stranded nucleic acid, or, alternatively, the total nucleic acid is adsorbed to the solid carrier.

A decisive difference of the present invention as compared with EP 1 146 049 B1 is, therefore, that the aqueous saline solution having a concentration greater than 1M—in the absence of alcohol—brings about the result that not the single-stranded nucleic acid (as in EP 1 146 049 B1) or the total nucleic acid, but exclusively the double-stranded nucleic acid is adsorbed onto the solid carrier. This result was surprising, and could not be derived from the state of the art.

In WO97/37040 A2, as well, high salt concentrations of complexing components (EDTA; EGTA) are required for binding of a double-stranded nucleic acid.

Thus, two different patents that describe the same goal explicitly point out that a complexing component (EDTA; EGTA) represent the essential component for binding of a double-stranded nucleic acid.

The present invention, however, surprisingly shows just the opposite effect, namely that binding of double-stranded nucleic acid is implemented in excellent manner specifically if no complexing agent is present. This effect could thus not have been expected in any way.

Accordingly, it has been shown that in the method according to the present invention, binding of double-stranded nucleic acid to a solid carrier material takes place under precisely the opposite binding conditions. Adsorption of the double-stranded nucleic acids takes place if the aforementioned saline solution contains no alcohol. In this case, it is also possible to do without substances that complex earth-alkali ions, or sarcosinates, or other washing, dispersion, or wetting agents, for adsorption of the double-stranded nucleic acids.

The method for parallel isolation of genomic DNA and cellular RNA is thus implemented by means of the method according to the present invention, as follows:

The source that contains nucleic acid is homogenized, if necessary, or lysed, whereby the lysis buffer contains a high salt concentration (>1M), but, in contrast to the patent EP 1146049, no alcohol, no substances that complex earth-alkali ions, and/or no washing, dispersion, or wetting agents. After homogenization/lysis, the solubilized sample is brought into contact with a solid carrier, preferably a mineral carrier material. In this connection, the carrier material can be supplied in different forms. In a preferred embodiment variant, the carrier material is a component of a mini-centrifugation column.

Under the conditions indicated, the genomic DNA (double-stranded nucleic acid) binds to the carrier material, but the RNA (single-stranded nucleic acid) does not. The filtrate contains the RNA and is saved for the further extraction process. The genomic DNA bound to the carrier material is subsequently washed with an alcoholic washing buffer, and finally eluted from the carrier material by means of a low-salt buffer or water. The saved filtrate, which contains the single-stranded nucleic acid, is mixed with an alcoholic solution and now also brought into contact with another mineral carrier material. Again, the mineral material can be present in the most varied forms, preferably again as a component of a centrifugation column. In this connection, the carrier material for binding of the RNA can be made from the same mineral material as for binding of the genomic DNA.

To increase the efficiency of binding of the RNA, the alcoholic solution can contain additional salts, if necessary, particularly sodium acetate buffer or potassium acetate buffer, having acid pH values, or an alcohol-detergent mixture, particularly non-ionic detergents (e.g. Tween20, Tween80, TritonX-100).

After binding of the RNA to the carrier material being used, known washing steps take place, if necessary. Finally, the RNA is also eluted from the carrier material by means of a low-salt buffer or by means of water.

By means of these extremely simple method sequences, DNA and RNA can be quickly and efficiently isolated from a biological sample.

In another embodiment alternative according to the present invention, highly pure cellular total RNA, which is substantially free of contaminating genomic DNA, (preferably completely free of contaminating genomic DNA) to the greatest possible extent, can also be isolated by means of the separation of double-stranded and single-stranded nucleic acid, in highly efficient and quick manner, so that the enzymatic DNA digestion steps that were previously used are no longer necessary.

For this purpose, the mechanism described according to the present invention, that of selective adsorption of double-stranded nucleic acid (DNA) to a mineral carrier material, is used, but no further work is carried out with the bound DNA. After removal of the genomic DNA from the starting sample, the latter is subsequently mixed, as described above, with an alcohol solution, which can contain additional salt components, if necessary, and this batch is brought into contact with another mineral carrier material, the carrier material with the bound RNA is washed with an alcoholic washing buffer, if necessary, and finally, the RNA is eluted from the carrier material by means of a low-salt buffer or by means of water. The method for selective isolation of highly pure RNA, substantially free of genomic DNA (preferably completely free of genomic DNA), is impressive in its rapidity and simplicity.

Interestingly enough, the same mineral materials can be used for specific binding of the two nucleic acid fractions. However, there is also the possibility of using different materials for the selective binding of DNA and RNA. Thus, for example, selective removal of the genomic DNA can take place quickly and efficiently, using a centrifugation column having a glass fiber material, whereby subsequently, binding of the RNA takes place after addition of the alcoholic component described, to magnetic iron oxide particles, preferably having modified surfaces. In this connection, a manual step for removing DNA from a biological sample, for example, is then combined with an automated method (e.g. automated magnetic particle separation), with the goal of quickly isolating highly pure RNA.

The nucleic acids (genomic DNA and/or RNA) isolated by means of the method variants according to the present invention are non-degraded and of excellent quality ($OD_{260}$: $OD_{280}$=1.8-2.0). The contamination with genomic DNA can be ignored, and this is possible without the enzymatic steps that were previously required (use of DNAse I).

The methods allow both parallel isolation of DNA and RNA and selective isolation of RNA from fundamentally any biological starting sample. In this connection, even extremely slight amounts of starting material can be made accessible to isolation. This is particularly significant when working with micro-dissected samples. Specifically in the case of these extremely limited sample amounts, parallel isolation of DNA and RNA is a significant advantage.

The present invention will be explained in greater detail below, using an exemplary embodiment, whereby the exemplary embodiment does not represent any limitation of the method according to the present invention.

EXAMPLE

Parallel Isolation of Genomic DNA and Cellular Total RNA from a Tissue Sample 20 mg of liver tissue of a mouse were transferred to a 1.5 ml reaction vessel. 450 µl lysis buffer were added (4 M guanidine thiocyanate, 80 mM tri-sodium citrate dehydrate). The tissue sample was ground-up using a micro-homogenizer. The sample was incubated for 30 min at room temperature. The lysis batch was transferred to a filter column having a collection vessel (glass fiber filter from the Whatmann company) and centrifuge for 2 min at 10,000×g. During this step, the genomic DNA bound to the surface of the filter column. The filter column with the bound DNA was inserted into a new collection vessel. The filtrate obtained contained the cellular total RNA and was mixed with an equal volume of 70% ethanol. This batch was then transferred to a filter column (glass fiber filter from the Whatmann company) having a collection vessel, and also centrifuged at 10,000×g for 1 min. The filtrate was disposed of, and the filter column with the bound RNA was inserted into a new collection vessel. The two filter columns were then washed with a washing buffer that contained ethanol (e.g. 80% ethanol, 50 mM NaCl, 10 mM tris HCl), and subsequently dried by centrifugation. Elution of the bound genomic DNA took place by adding 100 µl elution buffer (10 mM tris HCl) or water. Elution of the cellular total RNA took place by adding 100 μl of water free RNase. The two filter columns were centrifuged at 10,000×g for 1 min. The filter columns were disposed of. The filtrates contained the two nucleic acid fractions.

German patent application DE 10 2006 031 764.5 filed Jul. 6, 2006 and PCT/EP 2007/056879, filed Jul. 6, 2007, are incorporated herein by reference in their entirety.

Numerous modifications and variations on the present invention are possible in light of the above teachings. It is therefore to be understood that within the scope of the appended claims, the invention may be practiced otherwise than as specifically described herein.

The invention claimed is:

1. A method for separating double-stranded and single-stranded nucleic acids comprising:
    a) adjusting the salt content of a lysed or homogenized sample containing double-stranded and single-stranded nucleic acids with a non-chaotropic aqueous saline solution having a salt concentration greater than 1M until the double-stranded nucleic acids bind to a first solid carrier, but the single-stranded nucleic acids remain in solution; wherein said adjusting is performed without the addition of all of the following substances: alcohol, EDTA, and EGTA;
    b) removing the first solid carrier to which the double-stranded nucleic acids are bound; and
    c) recovering the single-stranded nucleic acid from the adjusted sample solution,
    wherein recovering the single-stranded nucleic acid from the adjusted sample solution comprises mixing it with an alcoholic solution containing 1 to 90 vol. % alcohol and contacting the resulting mixture with a second solid carrier that binds to single-stranded nucleic acids,
    wherein the alcoholic solution comprises an alcohol having 1 to 5 carbon atoms, and wherein the alcoholic solution comprises
    a) a sodium acetate buffer or a potassium acetate buffer, or
    b) an alcohol-detergent mixture.

2. The method according to claim 1, wherein a mineral carrier is used as first and/or second solid carrier.

3. The method according to claim 1, wherein first and/or second solid carrier is a component of a mini-centrifugation column.

4. The method according to claim 1, wherein the same material is used for adsorption of the double-stranded nucleic acid and for adsorption of the single-stranded nucleic acid.

5. The method according to claim 1, wherein the alcoholic solution comprises a sodium acetate buffer.

6. The method according to claim 1, wherein the alcoholic solution comprises a potassium acetate buffer.

7. The method according to claim 1, wherein the alcoholic solution comprises a detergent.

8. The method according to claim 1, wherein a mineral carrier or magnetic iron oxide particles are used as the solid carrier for adsorption of the single-stranded nucleic acid.

9. The method according to claim 1, wherein a mineral carrier or magnetic iron oxide particles having modified surfaces are used as the solid carrier for adsorption of the single-stranded nucleic acid.

10. The method according to claim 1, wherein pure cellular total RNA, which is substantially free of genomic DNA, is isolated from a mixture of cellular total RNA and genomic DNA, or from sources that contain cellular total RNA and genomic DNA, by binding the genomic DNA to the first solid carrier.

11. The method according to claim 1, wherein no phenol or chloroform are used.

12. The method according to claim 1, wherein step a) is carried out in the absence of all of the following: alcohol, EDTA, EGTA, a washing agent, a dispersion agent, and a wetting agent.

13. The method according to claim 1, which comprises the selective removal of a double-stranded nucleic acid that is genomic DNA from a mixture of a double-stranded genomic DNA and a single-stranded nucleic acid that is total cellular RNA.

14. The method according to claim 1, wherein said lysed or homogenized sample contains guanidine thiocyanate and/or trisodium citrate.

15. The method according to claim 1, wherein said adjusting is performed in the absence of any of alcohol, EDTA, EGTA, and sarcosinates.

16. The method according to claim 1, wherein said adjusting in step a) is performed in the absence of all of the following substances: alcohol, sarcosinates, EDTA, EGTA or another non-citrate substance that complexes earth-alkali ions.

17. The method according to claim 1, wherein step c) the concentration of alcohol in the solution ranges from 20-80% by volume.

18. The method of claim 1, further comprising separating double-stranded nucleic acids from the first solid carrier after removal of the single-stranded nucleic acids.

19. The method of claim 1, wherein said adjusting is performed without the addition of all of the following substances: alcohol, citrate, EDTA, and EGTA.

* * * * *